Figure 1:
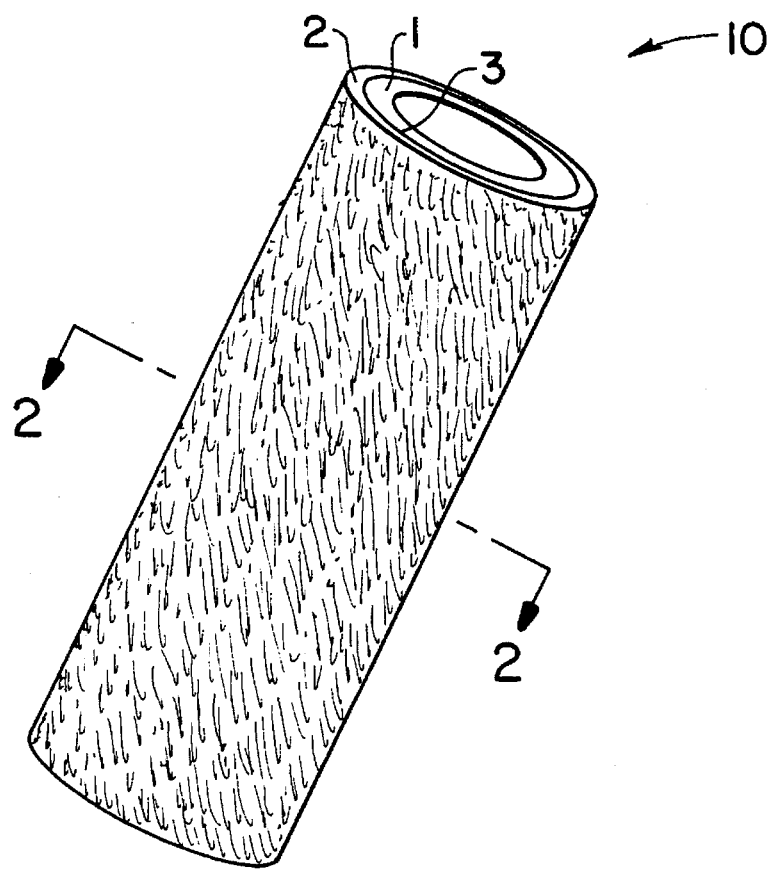

United States Patent [19]
Blott

[11] Patent Number: 5,474,525
[45] Date of Patent: Dec. 12, 1995

[54] TUBE MATERIALS

[75] Inventor: Patrick L. Blott, Bishops Stortford, United Kingdom

[73] Assignee: Smith & Nephew p.l.c., United Kingdom

[21] Appl. No.: 815,545

[22] Filed: Dec. 26, 1991

Related U.S. Application Data

[63] Continuation of Ser. No. 657,896, Feb. 19, 1991, abandoned, which is a continuation of Ser. No. 393,362, Aug. 14, 1989, abandoned.

[30] Foreign Application Priority Data

Aug. 13, 1988 [GB] United Kingdom .................. 8819311
May 23, 1989 [GB] United Kingdom .................. 8911808

[51] Int. Cl.$^6$ ................................................. A61F 13/00
[52] U.S. Cl. .................................. 602/63; 602/60; 602/41
[58] Field of Search ................................ 602/2, 3, 4, 40, 602/41, 42, 43, 44, 45, 46, 47, 60, 61, 76

[56] References Cited

U.S. PATENT DOCUMENTS

| | | | |
|---|---|---|---|
| 3,934,582 | 1/1976 | Gorrie | 128/856 |
| 3,935,355 | 1/1976 | Kuhn | 128/90 X |
| 3,990,437 | 11/1976 | Boyden, Jr. et al. | 264/171 X |
| 4,019,506 | 4/1977 | Eschmann | 128/90 |
| 4,084,586 | 4/1978 | Hettick | 128/165 X |
| 4,269,181 | 5/1981 | Delannoy | 128/165 X |
| 4,414,970 | 11/1983 | Berry | 128/156 |
| 4,479,490 | 10/1984 | Dedo | 128/91 R X |
| 4,832,010 | 5/1989 | Lerman | 128/165 |
| 4,841,958 | 6/1989 | Ersfeld et al. | 128/90 |
| 4,846,164 | 7/1989 | Martz | 128/156 X |

Primary Examiner—Sam Rimell
Attorney, Agent, or Firm—Rosenman & Colin

[57] ABSTRACT

A tubular undercast padding for a body immobilising cast comprises a conformable, elastically extensible material which material comprises a lofted non-woven fabric. The lofted non-woven fabric may be rendered extensible by forming as a folded or creped layer on a supporting layer of an elastically extensible material.

16 Claims, 1 Drawing Sheet

TUBE MATERIALS

This application is a continuation of Ser. No. 07/657,896, filed Feb. 19, 1991, now abandoned, which was a continuation of Ser. No. 07/393,362, filed Aug. 14, 1989, now abandoned.

The present invention relates to tube materials for use as an orthopaedic cast underpadding, such materials in combination with orthopaedic cast material and processes for the preparation thereof.

Treatment of bone deformities of the body such as bone fractures usually involves immobilisation of a portion of the body or body portion for example within a rigid cast made of plaster of Paris or a plastics material. Such rigid casts, which can remain on the body for one to two months, can cause discomfort and trauma to the patient. Trauma can be caused by the chaffing of those parts of the body, such as bony protruberances, which are placed under pressure by the cast. Such chaffing and pressure may lead to ulceration of the skin or tissue overlying a protruberance. To alleviate this problem it is now usual to apply an underpadding to the body portion prior to forming the cast to act as a cushion between the cast and the body. The underpadding commonly used for this purpose is a strip of fibrous wadding which can be wrapped around the body portion or over a tube of extensible knitted or woven stockinette previously applied over a body extremity onto the body portion.

In U.S. Pat. No. 4,479,490 an undercast padding for use with limb extremities is described, in the form of an outer sleeve of padding material and an inner sleeve of two way stretchable fabric.

The outer sleeve is provided with a flanged periphery at its distal end to prevent the plaster bandage, when applied, from extending beyond the extremity. When employed as an undercast for use with the hand, the sleeve is also provided with a lateral extension to accomodate the thumb, the distal end of the extension also being provided with a flanged periphery. A further feature, in the case of hand casts, is that the outer sleeve provided with a thickened region in the palmar region thereby to support the hand and maintain the transverse metacarpel arch during the setting of the casting plaster. The provision of flanges on the distal end of the outer sleeve, the provision of a lateral tubular extension and thickening in the palmar region adversely affect the overall flexibility of the underpadding and any flexibility in the outer sleeve is such as to permit only slight adjustment which in place on the limb. Although the material of the outer sleeve may be a flexible material such as a felt or a foam, the function of the sleeve is to support the limbs construction the sleeve per se would have an adverse effect on its flexibility.

The undercast may be applied either by first applying the stretchable inner sleeve followed by the outer sleeve or by inserting the inner sleeve into the cavity formed within the outer sleeve and applying both sleeves together. Registry of the sleeves can be maintained by securing the inner sleeve to an inner surface of the outer sleeve.

Such undercasts are intended for use with limb extremities only and therefore when more proximal parts of the limb also require splinting, conventional wadding strips have to be used in conjunction with the sleeves.

The present invention attempts to avoid the disadvantages of the prior art undercast paddings by providing a unitary tubular undercast padding which is elastically extensible, can be applied in a single operation, and can be employed in one piece as an undercast padding for all of the body portion which requires immobilisation.

The present invention therefore provides a composite tubular underpadding comprising a conformable, elastically extensible non-woven material.

In accordance with one aspect of the invention there is provided a tubular underpadding for a body portion immobilising cast comprising a conformable, elastically extensible material wherein said material comprises a lofted non-woven fabric.

The tubular underpadding of the invention will comprise an elastically extensible material to render it conformable to the body portion. The tube therefore can comprise an elastic component or components to provide this extensibility. Preferably such elastic component or components are located around the circumference of the tube thereby enabling it to be radially extensible or expandable.

The tubular underpadding of the invention thus is a tube of conformable elastically extensible material which can be adapted to expand or contract to allow it to be applied over a body extremity to a body portion and comprises a lofted non-woven fabric which is sufficiently thick to provide a cushion under the cast. Furthermore the tube can conform with the body portion when it swells or reduces in size during immobilisation under a cast.

The tubular underpadding of the invention can extend elastically in the width direction by 50% or more, suitably at least a 100% and can preferably extend elastically in the width direction by at least 120%. Such extension can be conveniently measured on the lay flat form of the tubular underpadding.

Figure 2:
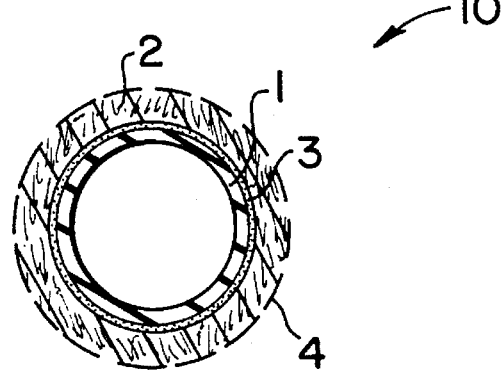

FIG. 1 schematically isometrically depicts the tubular underpadding of the present invention; and FIG. 2 is a cross section view taken along line 2—2 of FIG. 1, shown in dashed line relation to a outer disposed cast material.

A lofted non-woven fabric as used herein is a non-woven fabric having fibres lying in the direction of all three dimensions and of sufficient thickness to provide a cushion for an immobilising rigid cast on a portion of the body.

The material employed for the construction of lofted non-woven fabric can be natural or synthetic fibres of the type conventionally used, for example as a wadding, for orthopaedic cast underpaddings.

Such a wadding can comprise hydrophilic or hydrophobic fibres or blends thereof.

Suitable hydrophilic fibres include cellulosic fibres such as cotton and viscose rayon fibres. Hydrophilic fibres can advantageously provide the lofted non-woven fabric with softness to skin and the capacity to absorb perspiration.

Suitable hydrophobic fibres include polyester, polypropylene and high density polyethylene fibres. Hydrophobic fibres render the lofted non-woven fabric relatively non-absorbent so that water penetrating the fabric can drain away.

The lofted non-woven fabric can also comprise meltable fibres such as conjugated or bicomponent fibres of higher and lower melting points to bond the fibres in the fabric.

The non-woven fabric used in the invention can suitably have a thickness of 2 to 10 mm and preferably have a thickness of 3 to 8 mm. Similarly the non-woven fabric can suitably have a weight per unit area of 5 to 200 g/m$^2$.

The lofted non-woven fabric will preferably be formed in a manner to render the fabric resilient.

An apt resilient lofted non-woven fabric for use in the invention is hydrophilic fibres containing fabric marketed under the trade name SOFFBAN natural orthopaedic padding (Smith & Nephew Medical Ltd). Such a non-woven fabric comprises viscose rayon fibres, has a thickness of 3.6 to 4.2 mm and a weight per unit area of 105 to 140 g/m$^2$.

Another apt resilient lofted non-woven fabric for use in the is hydrophobic fibres containing fabric marketed under the trade name SOFFBAN synthetic orthopaedic padding (Smith & Nephew Medical Ltd). Such a non-woven fabric comprises a blend of polyester fibres (85%) and meltable conjugate fibres (15%) having a polypropylene core surrounded by a high-density polyethylene layer, has a thickness of 4.25 to 5.25 mm and a weight per unit of 75 to 100 g/m$^2$.

The layer of lofted non-woven fabric used in the invention can be in the form of a tube. The padding may therefore consist of a tube of conformable elastically extensible composite material comprising a lofted non-woven fabric. Such a tube can comprise two or more layers, a spiral strip (or helix) of lofted non-woven fabric or a unitary cylinder of the fabric.

In preferred embodiments of the invention the lofted non-woven fabric forms an outer layer of the tube which is attached to an inner support layer of extensible material.

The inner support layer can be a tubular fabric such as knitted stockinette or a woven or non-woven fabric tube which has been rendered elastically extensible as hereinafter explained.

Suitable stockinettes can comprise hydrophilic or hydrophobic fibres or mixtures comprising both such fibres. Hydrophilic fibres such as cellulosic fibres for example cotton or viscose fibres can render the support layer moisture absorbent. Hydrophobic fibres, however, can reduce the water absorbing or support layer.

The outer and inner layers can suitably be attached by any conventionally heat or adhesive bonding or by a mechanical method such as stitching.

The inner and outer layers of the medical padding tube are preferably adhered to each other by a layer of moisture vapour permeable adhesive. The adhesive may be a hot melt or pressure sensitive adhesive. A continuous layer of such an adhesive will advantageously also be impervious to liquids such as water.

Favoured moisture vapour permeable adhesives for this purpose are the polyvinyl ether and acrylate ester adhesives disclosed in United Kingdom Patent Nos. 1280631 and 2070631. An apt adhesive is a pressure sensitive adhesive copolymer of 47 parts by weight of n-butyl acrylate, 47 parts by weight of 2-ethyl hexyl acrylate and 6 parts by weight of acrylic acid made according to method disclosed in United Kingdom Patent No. 2070631.

The outer and inner layers can be heat bonded by means of a hot melt adhesive or interposed heat meltable layer.

A favoured hot melt or meltable adhesive comprises a thermoplastic polyurethane. An apt polyurethane of this type is known as Estane for example Estane 5712 available from BF Goodrich.

Suitable elastic or elastomeric components include elastic yarns conventionally used in elastic fabrics such as rubber or polyurethane threads or strips.

Preferred materials for use as the elastic component include elastomers which have Stretch Relaxed properties, i.e. are relaxed even when in a stretch condition. Such elastomers include styrene-butadiene-styrene copolymers sold under the Trade names Kraton or Cariflex.

The elastic component or components in an elastic tube of the invention can conveniently extend in a circular or helical fashion around the circumference of the tube.

The elastic component or components can be attached to or located within the lofted non-woven fabric. However, in embodiments of the invention which comprise an outer layer of lofted non-woven fabric and an inner layer of an extensible support material or fabric it is preferred that elastic component forms part of the support fabric or is attached to the outside of the support fabric so that it located between the inner and outer layers.

In favoured embodiments of the invention the inner support layer has as an elastic component an elastic thread or yarn which forms part of a woven or knitted tubular fabric or is attached to the outside these tubular fabrics or a tubular non-woven fabric.

As shown in FIGS. 1 and 2, the tubular underpadding 10 is comprised of inner elastic layer 1 and outer lofted non-woven fabric layer 2 adhered to each other by adhesive 3, positioned therebetween. As further shown in FIG. 2, cast material 4 is disposed about the outer portion of lofted non woven fabric 2.

Suitable elastic extensible woven or knitted tubular fabrics for use for the support layer include fabrics of the type normally used for elasticated tubular bandages such as those or modifications thereof specified in the British Phamacopia. Such elasticated tubular fabrics comprise a knitted fabric of ribbed structure containing a covered natural or synthetic rubber elastic thread or yarn aranged in a spiral fashion in the tube, Typical elastic yarns or threads are covered by crimped fibres and yarns spun from cotton or a blend of cotton and viscose fibres, The non-woven fabric used for the support layer may be a "two dimensional" non-woven fabric of the type used for cover layers on absorbent pads such as sanitary towels and diapers, Such non-woven fabrics advantageously have a soft feel to the skin, Tubes of these non-woven fabrics can be formed from a strip or sheet thereof in same manner as tube a of lofted non-woven fabric as hereinbefore mentioned.

In the tubular underpadding of the invention the non-extensible material or materials in the wall of the tube will suitably be compressed into folds such as axial i.e. circumferential undulating folds to render the tube extensible or expandible in at least the radial direction of the tube. The wall of the tube will therefore usually exhibit substantially axial crepe, crinkled or undulated fold pattern. Although the density of these folds will reduce as the tube is expanded, such folds can advantageously increase the thickness and thereby the cushioning of the layer when used as an orthopaedic padding. Such a creped layer of lofted non-woven fabric is preferably adhered to a supporting layer of an elastically extensible material.

The tubular underpadding of the invention can be adapted in size to the size of the body portion to be immobilised by the cast.

A feature of the invention therefore is that the undercast padding can be readily stretched to pass over and around the body portion. Although the underpadding is highly stretchable when it is located over the body portion it will relax and conform to the body shape and because of its construction the lofted non-woven fabric will re-assume, or nearly re-assume its original bulk shape.

In a further aspect the present invention provides of process of forming a tubular Underpadding of the invention which comprises attaching a layer of lofted non-woven fabric to an elastic component.

The elastic component preferably forms part of an elastic extensible tubular support fabric. Thus preferred processes of the invention comprise attaching an outer layer of lofted non-woven fabric to an inner support layer of tubular elastically extensible fabric.

In the process of the invention the lofted non-woven fabric layer can be provided with axial folds such as axial undulating folds to render the layer extensible prior to, during or after it attached to inner support layer of tubular elastically extensible fabric.

Prior to attachment the lofted non-woven fabric layer can be embossed or compressed to provide the undulating folds. The undulating folds in the layer can also be provided by bonding, for example by adhesive or heat bonding the layer in a folded form to discrete linear areas of the inner layer. In a preferred process of the invention the outer layer of lofted non-woven fabric is attached to an expanded inner layer of tubular elastic fabric and the composite layered tube allowed to contract. In such a process the composite tube is provided with an undulating folds in the axial direction thereof.

The tubular fabric can be expanded radially or widthwise in a substantially flat or collapsed form. The tubular fabric can conveniently be radially expanded over a mandrel of suitable size.

The tubular fabric can be expanded widthwise in a substantially flat state by means of a stenter for example a clip or pin stenter or passage around one or more stretching plates, for example one of a pair of such plates, preferably provided with tapered leading and trailing sides.

The tubular fabric can be an elastic fabric for example a woven or knitted fabric which comprises an elastic thread in its circumference. Alternatively the tubular fabric can be a tubular knitted fabric or a non woven fabric formed from a strip or sheet which has been rendered elastic by attaching tensioned elastic thread or threads in a circular or spiral fashion around the outside of the inner layer.

In a preferred process of the invention the outer surface of the inner layer of tubular fabric containing or attached to the elastic component or components is provided with adhesive and the outer layer of lofted non-woven fabric strip or sheet is attached to inner layer by the adhesive. The adhesive can be provided prior or after expansion of the tubular fabric by any convenient coating method such as a solvent, hot melt or transfer coating method or by use of an adhesive coated strip component when forming the inner tubular fabric.

A preferred adhesive coating method for use in the process is a hot melt adhesive coating method using for example a spray or roller coating head. When such a method is employed during a process in which the tubular fabric is expanded widthwise in a flat form the hot melt adhesive will be coated on both outer surfaces of the flattened tubular fabric. The hot melt adhesive can advantageously be coated prior to expansion of the tubular fabric to inhibit penetration of the adhesive through the fabric such as stockinette fabric. In such a process the lofted non-woven fabric strip or sheet can be conveniently laminated to the adhesive coated surfaces of the expanded flat tubular fabric by passage through the nip of two pressure rollers. The rollers can be adapted to be heated facilitate the adhesive bonding or alternatively cooled to inhibit permanent compression of the lofted non-woven fabric. A second set of pressure roller if necessary may also be provided.

When the tubular fabric inner layer is expanded on a rotatable such as a driven rotatable mandrel, the adhesive, elastic or non-woven fabric components in thread or strip form can conveniently be applied around the inner layer while the mandrel is rotating. The tension in an elastic thread which is spirally wound around such a rotating mandrel can be adjusted by controlling the speed at which the elastic thread is fed into the mandrel.

The expanded elastic composite layered tube can then be removed from the stenter, mandrel or plate allowed to contract.

The undercast paddings of the invention will suitably be employed in combination with a body portion immobilising cast.

Thus the present invention further provides a splinting system comprising, in combination a tubular undercast padding in accordance with the invention and a casting material for immobilising body portions.

Although the tubular undercast paddings may be employed with any known casting materials, including plaster of Paris, suitable casting materials for use with the under padding are synthetic casting or splinting materials such as those based on polyurethane resins. Such casting materials are available as a resin impregnated bandaging substrate. Once wetted with water the resin will cure and set.

Suitable polyurethane casting materials for use in combination with the tubular undercast paddings of the invention include those described in U.S. Pat. No. 4,427,002, 4,427,002 and 4,574,793.

Substrates for the resin are well known and can include materials such as glass fibre.

In yet a further aspect of the invention there is provided a method of immobilising a body portion including the steps of applying an underpadding in accordance with the invention and thereafter applying an immobilising cast onto the underpadding. The casting material employed in this method may be as hereinbefore described.

The invention will now be illustrated by reference to the following examples.

EXAMPLE 1

A tube of the invention was prepared by mounting a conventional tubular knitted cotton stockinette in an expanded state over mandrel (diameter 204 mm) connected to motor. An adhesive layer (25 g/m$^2$) was transfer coated from silicone release paper onto the outer surface of stockinette and tensioned elastic rubber thread spirally wound (space between turns 2 cm) onto the adhesive surface of the stockinette.

The adhesive used was a pressure sensitive adhesive copolymer of 47 parts by weight n-butyl acrylate 47 parts by weight of ethyl hexyl acrylate and 6 parts by weight of acrylic acid. The tension of elastic thread was obtained by feeding the thread from a roll which was driven at a lower surface speed than that of the mandrel. A strip (width 6 cm) of lofted non-woven fabric was then spirally wound over the elastic thread and the adhesive surface of the stockinette. The expanded tube was then removed from the mandrel and allowed to elastically contract to form crinkled walls. The tubular padding had a length of 29 cm and a diameter of approximately 6.4 cm which could be elastically expanded to a diameter of 14.6 cm.

The lofted non-woven fabric used in this example comprised heat bonded polyester fibres and had a weight per unit area of 85 g/m$^2$ and a thickness of approximately 5 mm. The drawing schematically depicts, in section and in enlarged scale, a tube 1 formed according to Example 1, comprising a tubular knitted cotton stockinette 2, adhesive layer 3, elastic rubber threads 4 and lofted non-woven fabric 5.

EXAMPLE 2

A tube was formed in the same manner as Example 1 except that an inner tube of spirally wound non-woven fabric (Spun bonded polyester fibres available from Asahai) was used in place of the stockinette. The medical padding had length of 20 cm and diameter of 5.7 cm which could be expanded to diameter of 12.1 cm.

EXAMPLE 3

A tube of the invention was prepared by mounting and stretching a tubular elastic stockinette (length 100 cm, lay-flat width 7.5 cm) over a flat plate former (length 125 cm, width 25 cm) of general rectangular shape with curved ends.

The stockinette was a modified elasticated rib knitted tubular bandage (Tensogrip available from Smith & Nephew) containing cotton/viscose fibres and covered rubber threads spirally knitted into the fabric.

The outer surface of the stockinette was then sprayed with a thermoplastic polyurethane (Estane 5712 available from BF Goodrich) adhesive solution in methylene chloride and dried to give a weight per unit area of $13\pm3$ g/m$^2$. The coating was then covered with release paper and heated (temperature 125° C.) under pressure to firmly anchor the polyurethane adhesive to the stockinette. A strip (of sufficient size) of lofted non-woven fabric (SOFFBAN SYNTHETIC) was heat laminated under pressure to cover the adhesive coated surface (after removal of the release paper therefrom) of the stockinette on both sides of the former by feeding the stockinette (on the former) and the non-woven fabric through the nip of two cool pressure rollers whilst heating the side of the former at which the non-woven fabric is laminated. The laminated tube so formed was removed from the former and was then cut in 30 cm lengths to provide elastic extensible tubular underpadding suitable for use with a wrist or lower arm cast or splint.

The tubular under padding had a lay flat width (internal) of approximately 10 cm and could be elastically stretched to a width of 25 cm.

It was found that when the tubular underpadding was in a fully or partially contracted state, for example in place on a arm or wrist, the lofted non-woven fabric layer exhibited an axial undulated fold pattern which advantageously increased the thickness and cushioning of the layer in use.

I claim:

1. A composite tubular underpadding comprising a conformable, elastically extensible material which comprises a non-woven fabric, wherein said underpadding comprises a lofted non-woven fabric and an elastic component.

2. A composite tubular underpadding comprising a conformable, elastically extensible material which comprises a non-woven fabric wherein the material comprises a lofted non-woven fabric in the form of a tube.

3. An underpadding according to claim 2 in which the lofted non-woven fabric is a radial extensible tubular layer containing undulating folds.

4. An underpadding according to claim 1 in which the lofted non-woven fabric forms an outer layer of the tube and is attached to an inner support layer of extensible material.

5. An underpadding according to claim 4 in which an elastic component forms part of the inner support layer.

6. An underpadding according to claim 5 in which the inner support layer is woven or knitted tubular fabric comprising elastic yarn.

7. An under padding according to claim 1 in which an elastic component is incorporated into or onto the lofted non-woven fabric.

8. An underpadding according to claim 5 wherein the elastic component is an elastomer.

9. An underpadding according to claim 5 wherein the elastic component is in the form of a thread or yarn.

10. A composite tubular underpadding comprising a conformable, elastically extensible material which comprises a non-woven fabric wherein the underpadding comprises an outer extensible layer of a lofted non-woven fabric, an inner extensible support layer and an elastic component between the outer and inner layers.

11. An underpadding according to claim 4 in which the layers are adhesively bonded.

12. A composite tubular underpadding comprising a conformable, elastically extensible material which comprises a non-woven fabric which underpadding is radially elastically extensible by at least 100%.

13. A splinting system comprising a tubular underpadding comprising a conformable, elastically extensible material which comprises a non-woven fabric in combination with a casting material for immobilising a body portion.

14. A system according to claim 13 wherein the casting material comprises a polyurethane resin.

15. A method of immobilising a body portion which comprises applying to said body portion a tubular undercast padding comprising a conformable, elastically extensible material which comprises a non-woven fabric and thereafter applying a casting material onto the underpadding and allowing the casting amterial to set.

16. An underpadding according to claim 1 in which the lofted non-woven fabric is a radial extensible tubular layer containing undulating folds.

* * * * *